United States Patent [19]
Saito et al.

[11] Patent Number: 4,685,802
[45] Date of Patent: Aug. 11, 1987

[54] SMALL PARTICLE DETECTION SYSTEM

[75] Inventors: Susumu Saito, Hachioji; Michio Suzuki, Hino; Kyo Suda, Hachioji; Yasuo Yatsugake, Odawara; Kazuya Tsukada, Oiso, all of Japan

[73] Assignees: Hitachi, Ltd., Tokyo; Hitachi Electronics Engineering Co. Ltd., Kanagawa, both of Japan

[21] Appl. No.: 721,904

[22] Filed: Apr. 10, 1985

[30] Foreign Application Priority Data

Apr. 11, 1984 [JP] Japan ............................... 59-70885
Nov. 9, 1984 [JP] Japan ............................... 59-234911

[51] Int. Cl.⁴ ........................................... G01N 21/00
[52] U.S. Cl. ..................................... 356/339; 356/352
[58] Field of Search ............... 356/336, 337, 338, 339, 356/352

[56] References Cited

U.S. PATENT DOCUMENTS

| | | | |
|---|---|---|---|
| 3,785,735 | 1/1974 | Friedman et al. | 356/339 X |
| 4,053,229 | 10/1977 | McCluney | 356/339 X |
| 4,571,079 | 2/1986 | Knollenberg | 356/339 X |

*Primary Examiner*—Eugene R. LaRoche
*Assistant Examiner*—Steven J. Mottola
*Attorney, Agent, or Firm*—Antonelli, Terry & Wands

[57] ABSTRACT

In a small particle detection system for use in detecting small particles, which float in a gas, by utilizing the light scattering effect thereof, a detecting cell is disposed in an external optical resonator which is adapted to resonate with the output light from a laser oscillator. When the detecting cell is disposed in the laser oscillating optical resonator, the position is selectively determined; the former is set in the position in the latter in which the diameter of a laser beam is minimal.

8 Claims, 9 Drawing Figures

SMALL PARTICLE DETECTION SYSTEM

BACKGROUND OF THE INVENTION

This invention relates to a small particle detection system using a light scattering method in which small particles floating in the air are detected by measuring the scattered light therefrom.

The techniques for measuring the small particles contained in a sample air stream, by applying a beam of light to the sample air stream to detect the scattered light therefrom are generally known. In order to improve the detecting performance in such techniques, it is effective to improve the intensity of the beam of light in use. Accordingly, a laser oscillator is used as a light source instead of a lamp. These systems are disclosed in, for example, "O plus E", December 1982 issue, page 78. In order to improve the detecting performance in these systems, it is effective to improve the intensity of the beam of light in use. Therefore, a high output power laser device for increasing the level of the laser output, or a system for passing sample aerosol through the laser resonator is used. The former causes the dimensions of the detecting system and the level of input electric power to increase. In the latter, the diameter of a laser beam from the laser resonator is determined depending upon the laser oscillating conditions, and the diameter of the beam in the position of a detecting cell is not necessarily set to an optimum level for the measurement of the scattered light. In addition, the degree of freedom of arranging the detecting cell is restricted.

The latter system, i.e. the system in which a sample air stream is introduced into a laser resonator so as to be irradiated with a laser beam therein, for making effective use of a laser beam is disclosed in "The Review of Scientific Instruments", Vol. 39, No. 12, page 1916, or Vol. 44, No. 9, page 1193. In this system, a laser beam of a high intensity can be utilized even in a comparatively small-sized laser device. The relation between the laser oscillator and sample air stream detecting space in this system is as illustrated in FIGS. 1(*a*) and 1(*b*). Referring to the drawings, reference numeral 1 denotes a laser discharge tube, 2 a laser beam in the resonator, 3 a sample air stream ejected across the laser beam, and 4 the scattered signal light from the small particles contained in the air stream. In the system of FIG. 1(*a*), a spherical mirror 5 is disposed as a mirror for the laser resonator at one end thereof, a planar mirror 6 in the measurement space at the other end thereof, so as to reduce the diameter of the beam. In the system of FIG. 1(*b*), planar mirrors or spherical mirros of a comparatively large radius of curvature are used as reflecting mirrors 7, 8 at both sides, and the diameter of a beam in a resonator is nearly constant. In both of these systems, the diameter of the laser beam in the detecting space is large, and the laser beam is not utilized effectively with respect to the energy density thereof. Since the diameter of the laser beam in the detecting space is large, the light-scattering space becomes large, so that the quantity of the Rayleigh scattered light from the molecules of gases, such as $N_2$ and $O_2$ in this space increases. Hence, a satisfactory signal-noise ratio cannot be obtained during the measurement of small particles of a low density and a diameter of not more than about 0.1 μm. In the system of FIG. 1(*a*), the diameter of the beam can be set minimal on the surface of the mirror 6 but it is impossible in practice to provide a detecting space immediately before the mirror 6. Using the system with a laser beam focused on the mirror surface is liable to cause the mirror surface to be deteriorated. The mirror surface is influenced easily by the local soiling thereof and the intensity of the laser beam applied to such a mirror surface is apt to fluctuate.

SUMMARY OF THE INVENTION

An object of the present invention is to provide a small particle detection system which has solved the above-mentioned problems of a prior art system of this kind, and which has a stable and highly-improved performance.

Another object of the present invention is to provide a small particle detection system having a high detecting performance, which has solved the above-mentioned problems of a prior art system of this kind, and which has a combination of a laser oscillator structure suitable for the detection of scattered light and a detecting cell suitable for the oscillator structure and containing a sample air stream.

In order to achieve the above objects, the present invention is provided with an external optical resonator adapted to resonate with the laser from a laser oscillator and having a detecting cell therein.

In order to achieve the above objects, the present invention is provided with an external mirror laser resonator constituting a laser oscillator and containing a detecting cell therein, the laser resonator being formed so that a laser beam has the smallest cross-sectional area therein, the sample air stream and the laser cross each other in the position in which the laser beam has the smallest diameter.

BRIEF DESCRIPTION OF THE DRAWINGS

FIGS. 1*a* and *b* are a construction diagram of laser resonators which have heretofore been used for the detection of small particles;

FIGS. 2*a* and *b* are a sectioned side elevation and a sectioned plan of an embodiment of the present invention;

FIGS. 3 and 4 are schematic sectional views of other embodiments of the present invention;

FIG. 5 is a construction diagram of a laser resonator used in the present invention; and FIGS. 6*a* and *b* are a construction diagram of a further embodiment of a detection system according to the present invention.

DETAILED DESCRIPTION OF THE INVENTION

In order to achieve the above object, the present invention is provided with a laser oscillator, an external optical resonator adapted to resonant with the laser from this oscillator, and a detecting cell placed in this optical resonator. The detecting cell consists of nozzles for sucking and discharging a sample aerosol, an optical system for condensing the scattered light from the sample aerosol, and a light-detecting element for the photoelectric conversion of the condensed scattered light. A combination of all of the detecting cell, laser oscillator and external optical resonator constitutes a small particle detection system using a light scattering method. In this system, the optical path and the path of aerosol in the optical resonator cross each other.

Owing to such an arrangement, the intensity of light in the external optical resonator becomes substantially equal to that in a laser resonator, and, moreover, the diameter of a laser beam crossing an aerosol stream can be arbitrarily varied, so that the detection system as a whole can be optimized. Since the laser oscillator can be sealed perfectly, it is unnecessary to be concerned about the soiling of a laser oscillating mirror and the terminal surfaces of a laser medium, and a laser output is stable at all times. The external resonator consists of a Fabry-Pérot type resonator formed of two mirrors disposed in opposition to each other. One of these mirrors has a high and substantially perfect reflectivity with respect to the laser. The other mirror consists of a highly-reflective mirror having a partial transmittance so that a part of the laser passes therethrough. It is also possible that a mirror on the laser output side is used instead of the mirror of a partial transmittance with a highly-reflective mirror disposed in opposition thereto. In such an arrangement, the external resonator can be formed independently of the oscillating conditions for the laser. The curvature of the mirror in the external resonator can be set selectively to a suitable level so as to increase the intensity of scattered light, or a laser beam focusing lens can be disposed in the resonator. Accordingly, the distribution of the intensity of light in the resonator can be varied, so that more efficient measurement can be conducted.

In order to achieve another object of the present invention, a detecting cell is provided in an external mirror laser resonator which constitutes a laser oscillator.

The detecting cell consists of nozzles for sucking and discharging sample air thereinto and therefrom, an optical system for condensing the scattered light from the sample air, and a light-detecting element for the photoelectric conversion of the condensed scattered light.

The present invention is characterized in that the resonator is formed so that the cross-sectional area of a laser beam becomes minimal in the interior thereof, and the detecting cell is disposed so that the sample air stream and laser beam cross each other in the position in which the diameter of the laser beam becomes minimal.

A minimum diameter (2Wo) of a beam in the laser resonator is determined by an optical resonator length d, radii $R_1$, $R_2$ of curvature of mirrors at both ends, and oscillation wavelength $\lambda$ of the laser as shown in FIG. 5, and expressed by the following formula (cited from H. Kogelnik, T. Li: Appl. Opt. 5, 1550 (the year 1966)).

$$W_o^4 = \left(\frac{\lambda}{\pi}\right)^2 \frac{d(R_1 - d)(R_2 - d)(R_1 + R_2 - d)}{(R_1 + R_2 - 2d)^2} \quad (1)$$

Let $t_1$, $t_2$ equal the distance between the position in which the diameter of a beam becomes minimal with the mirrors $R_1$, $R_2$ at both ends. The following formulae can be established.

$$t_1 = \frac{d(R_2 - d)}{R_1 + R_2 - 2d} \quad (2)$$

$$t_1 + t_2 = d \quad (3)$$

The laser-oscillatable combinations of mirrors are (i) a combination of $d < R_1 < R_2$, and (ii) a combination of $d > R_1 > R_2$ and $R_1 + R_2 > d$. In all of these combinations, a position in which the diameter of a beam becomes minimal exists in an area which is on the side of the mirror $R_2$ with respect to the central portion of the resonator. The detecting cell is placed in this position, and the sample air stream and laser beam are sent forth so as to cross each other in the same position. The intensity of scattered light in this position is measured to detect small particles. If the cross-sectional area of the laser beam in the resonator is set in accordance with a generally-obtained TEMoo mode (Gaussian distribution shape), the diameter of the laser beam is defined at a point at which the intensity of the laser beam decreases to $e^{-2}$ of the central intensity. The diameter of a beam of sample air is determined by that of the nozzles provided in the detecting cell.

When the diameter and density of particles are small and low, respectively, the scattered signal light at a peripheral portion of a Gaussian beam is very weak to cause a detection error to occur. Therefore, it is necessary that the diameter of a laser beam be set larger than that of a beam of sample air. It is ideal that the diameter of a beam of sample air be set to not be higher than a level which is determined by a full width of half maximum of laser beam intensity (in this case, the ratio of the diameter of the laser beam to that of the air beam is not more than 1.7) but, if the diameter of the air beam is not more than that of laser beam, it poses no problems in practice even under extreme measuring conditions.

Since this detection system is constructed as described above, the intensity of the laser beam in the laser resonator can be utilized to the utmost, and the light-scattering space can be minimized. Accordingly, the signal-to-noise ratio can be improved, and the detection of small particles can be carried out with a high-sensitivity detection system. Since the diameter of the beam of the air stream with respect to that of the laser beam is set to an optimum level, the detection of particles can be conducted with a high accuracy. Moreover, since the intensity of laser beam on the resonator surface decreases, the deterioration of the mirror surface can be prevented, and the influence of the soiling thereof can be minimized. This enables a highly-reliable small particle detection system to be obtained.

DETAILED DESCRIPTION OF PREFERRED EMBODIMENTS

Figure 1A:
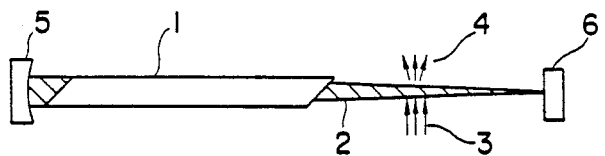
Figure 1B:
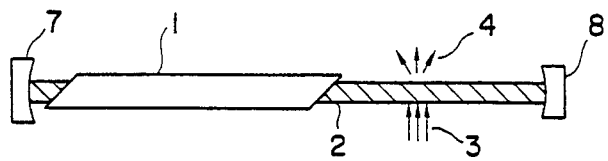
Figure 2A:
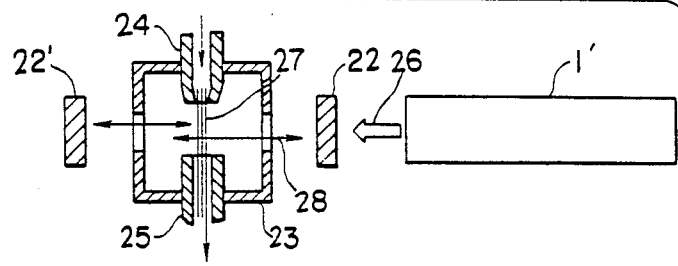
Figure 2B:
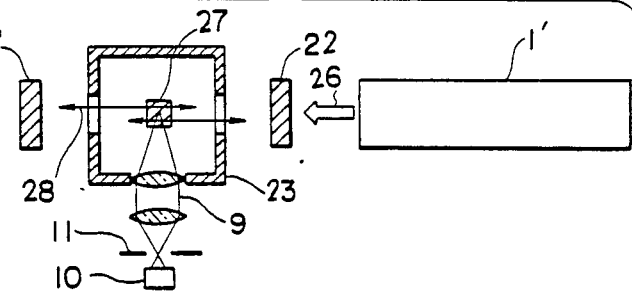

FIG. 2 is a schematic section of an embodiment of a small particle detection system using a light scattering method according to the present invention, wherein FIG. 2(a) is a sectioned side elevation; and FIG. 2(b) a sectioned plan. The output laser 26 from a laser oscillator 1' is introduced into a Fabri-Pérot optical resonator consisting of mirrors 22, 22' which are disposed in opposition to each other. The mirror 22 consists of a mirror with partial transmittance adapted to pass the output laser 26 therethrough and reflect the light from the mirror 22'. The laser 28 entering the resonator is reflected on the mirrors 22, 22' repeatedly. During this time, the intensity of light in the optical resonator resonated with the laser is substantially equal to that in the laser oscillator if the optical loss at the mirrors is ignored. A detecting cell 23 is provided in the optical resonator, and sample aerosol 27 is introduced from an inlet nozzle 24 thereinto so as to cross the laser beam 28, the sample aerosol 27 being discharged from an exhaust nozzle 25 to the outside of the detecting cell. During this time, small particles contained in the aerosol scatter the laser. This scattered light is condensed by an optical system 9 consisting of condenser lenses, and then converted into an electric signal by an optical detector 10.

A slit 11 is provided so as to eliminate the unnecessary stray light and thereby improve the S/N ratio.

Figure 3:
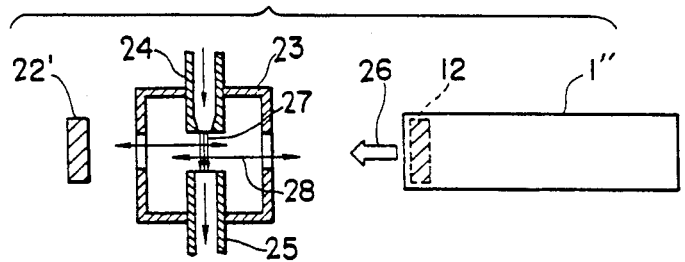

Another embodiment of the present invention is shown in FIG. 3. In this embodiment, an optical resonator is constituted by a mirror 12 provided in an output portion of a laser oscillator 1″, and another mirror 22′, and a detecting cell is placed in this resonator. This arrangement enables the particle detecting system to be simplified. The illustration of an optical detecting system is omitted.

Figure 4:
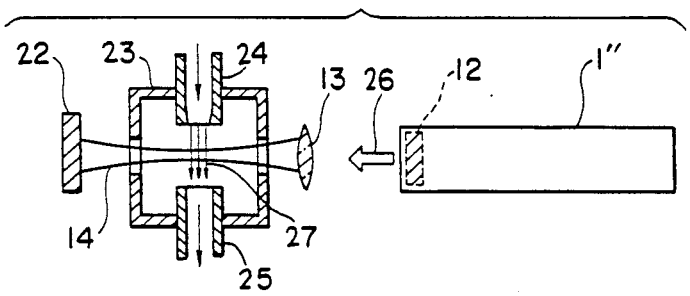
Figure 5:
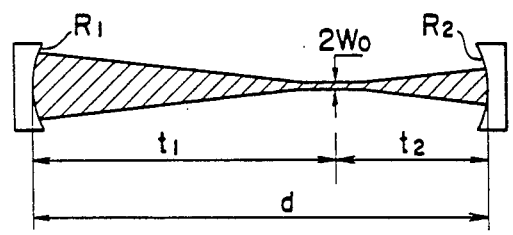

FIG. 4 shows still another embodiment of the present invention, The output light 26 from a laser source is focused by a lens 13 so that the light 26 crosses an aerosol stream 27 at an optimum diameter portion of the beam 14 of the light 26. The optical resonator in use consists of laser resonating mirror 12 in the oscillator 1″ and another mirror 22. Owing to the detecting cell of such construction, the small particle detecting accuracy can be improved. The lenses can also be combined with the optical resonator in the embodiment of FIG. 2.

According to this embodiment, the detecting sensitivity which is as high as that of the system in which a detecting cell is disposed in a laser resonator can be attained, and the degree of freedom of disposing the detecting cell increases. Moreover, the diameter of the laser beam can be controlled without varying the oscillating conditions for the laser oscillator. Accordingly, the laser output becomes stable, and a small particle detection system having a large practial effect can be obtained.

Figure 6A:
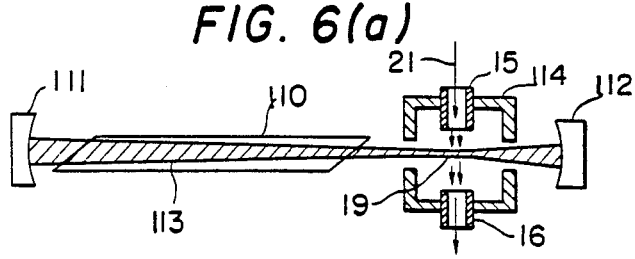
Figure 6B:
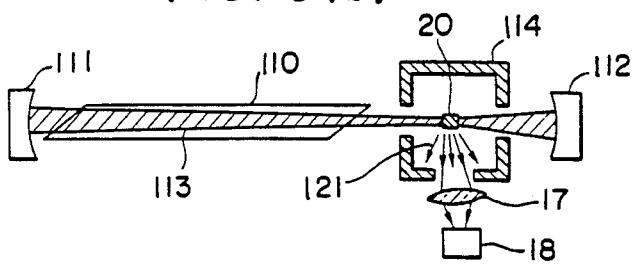

A further embodiment of the present invention will now be described with reference to FIG. 6. FIG. 6(a) is a side elevation, and FIG. 6(b) a plan. Mirrors 111, 112 having different radii of curvature and high reflectivities are disposed at both ends of a laser discharge tube 110 so as to constitute a laser resonator. The radii of curvature of the mirrors 111, 112 are determined in accordance with the formulae (1)–(3) above. In this embodiment, a detecting cell 114 is disposed so that a sample air stream 21 crosses a laser beam 113, which occurs in the resonator, at a point 19 at which the diameter of the beam 113 is minimal. Reference numerals 15, 16 denote inlet and exhaust nozzles provided in the detecting cell and formed so as to generate an air beam the diameter of which is substantially around ⅔ of that of the laser beam.

The scattered signal light 121 occurring in a light-scattering space 20 due to the small particles contained in a sample air stream 21 is condensed by a condenser lens 17 and detected by an optical detector 18. The measurement of the small particles is thus conducted.

In a practical example using a He-Cd laser discharge tube as a laser discharge tube 110 with the length of the discharge tube, the resonator length, the radius of curvature of a mirror 111 and the radius of curvature of a mirror 112 set to 60 cm, 100 cm, 1.5 m and 5 m, respectively, the oscillating wavelength of the He-Cd laser is 442 nm. Accordingly, the position in which the diameter of the laser beam is minimal is 11 cm away from the mirror 112. The diameter of the laser beam in this position is 640 um, and the diameter of the beam of a sample air stream, which crosses the laser beam, is kept smaller than the minimum diameter of the laser beam, for example, 430 um which is about ⅔ thereof. If the detection system if formed in this manner, the dimensions of the light-scattering space can be set to a required minimum level, and, moreover, a highly-intense laser beam can be applied to a sample air stream.

It is clear that the resonator can be formed variously in accordance with the results of calculations based on the formulae (1)-(3). Besides He-Cd, a gas laser, such as Ne, Ar and Kr, or various soled state lasers and dye lasers are used as necessary as a laser medium.

In the above embodiments, the detection of small particles in a gas is described. It is needless to say that the present invention can also be applied to the detection of small particles in a liquid in the same manner.

According to the embodiment described with referring to FIG. 6, the intensity of a laser beam in the laser resonator can be increased to the highest possible level, and this laser beam can be utilized effectively. Also, the dimensions of the light-scattering space can be restricted to a required minimum level, and a signal-to-noise ratio can be increased. Therefore, small particles can be detected by a highly-sensitive detection system.

Since the diameters of the laser beam and the sample air stream are set to optimum levels, small particles can be detected with a high accuracy. This enables the production of a small particle detection system which is capable of very accurately detecting small particles having a particle size of not more than 0.1 μm and a low density. Moreover, the deterioration of the laser mirrors and the influence of the soiling thereof can be prevented, so that a highly-reliable detection system can be provided.

We claim:

1. A small particle detection system comprising a laser oscillator, an external optical resonator adapted to resonate with an output from said laser oscillator, a detecting cell containing therein a sample stream, and an optical detecting element adapted to convert the scattered light from said sample stream into an electric signal, said detecting cell being disposed in said external optical resonator.

2. A small particle detection system according to claim 1, wherein one of mirrors which constitute said external optical resonator is used also as a mirror constituting said laser oscillator.

3. A small particle detection system according to claim 1 or 2, wherein a lens for varying the diameter of a laser beam is provided in said external optical resonator.

4. A small particle detection system comprising a laser oscillating optical resonator containing a laser active medium therein and providing a laser beam therein of varying diameter therealong, a detecting cell containing therein a sample stream, and an optical detecting element adapted to convert the scattered light from said sample stream into an electric signal, said detecting cell being disposed in the position in said optical resonator in which the diameter of the laser beam is minimal.

5. A small particle detection system according to claim 4, wherein the diameter of said sample stream is set no greater than a minimum diameter of the laser beam.

6. A small particle detection system according to claim 1, wherein said sample stream is one of a sample sol stream and a sample aerosol stream, said detecting cell being disposed in said external optical resonator so as to enable intersecting of one of said sample sol stream and sample aerosol stream with a laser beam output from said laser oscillator in said external optical resonator.

7. A small particle detection system according to claim 4, wherein said sample stream includes one of a sample sol stream and a sample aerosol stream, one of said sample sol stream and said sample aerosol stream intersecting with the laser beam in said optical resonator at the position in said optical resonator in which the diameter of the laser beam is minimal.

8. A small particle detection system according to claim 1, wherein said laser oscillator provides therein laser beam light of a first intensity, and said external optical resonator resonates with the output laser beam light of said laser oscillator and provides an intensity of the laser light beam therein substantially equal to the first intensity.

* * * * *